United States Patent [19]

Stapleton et al.

[11] Patent Number: 5,346,672
[45] Date of Patent: Sep. 13, 1994

[54] DEVICES FOR CONTAINING BIOLOGICAL SPECIMENS FOR THERMAL PROCESSING

[75] Inventors: Marilyn J. Stapleton, Durham; Villette S. Thorpe, Goldsboro; Warren R. Jewett, Cary, all of N.C.

[73] Assignee: Gene Tec Corporation, Durham, N.C.

[21] Appl. No.: 25,093

[22] Filed: Mar. 2, 1993

Related U.S. Application Data

[60] Continuation-in-part of Ser. No. 836,348, Mar. 3, 1992, and a continuation-in-part of Ser. No. 855,318, Mar. 23, 1992, Pat. No. 5,281,516, and a continuation-in-part of Ser. No. 929,720, Aug. 12, 1992, abandoned, which is a division of Ser. No. 438,592, Nov. 17, 1989, Pat. No. 5,188,963.

[51] Int. Cl.⁵ .............................. B01L 3/00
[52] U.S. Cl. ................................ 422/102; 422/99; 435/287; 435/290
[58] Field of Search ............... 422/99, 102, 103, 104, 422/436, 435; 436/177, 178; 435/287, 289, 290

[56] References Cited

U.S. PATENT DOCUMENTS

| | | | |
|---|---|---|---|
| 4,151,253 | 4/1979 | Waggoner et al. | 422/102 |
| 4,647,431 | 3/1987 | Sekine et al. | 422/99 X |
| 4,777,020 | 10/1988 | Brigati | 422/99 |
| 4,814,279 | 3/1989 | Sugaya | 422/104 X |
| 4,935,374 | 6/1990 | Jacobs et al. | 422/99 X |
| 4,952,498 | 8/1990 | Waters | 435/291 X |
| 4,952,516 | 8/1990 | Matkovich | 422/102 X |
| 4,963,333 | 10/1990 | Shaw et al. | 422/99 |
| 4,981,805 | 1/1991 | Yazawa et al. | 422/102 X |
| 4,986,964 | 1/1991 | Carr, Jr. et al. | 422/73 |
| 5,188,963 | 2/1993 | Stapleton | 435/299 |
| 5,192,503 | 3/1993 | McGrath et al. | 422/99 X |

Primary Examiner—James C. Housel
Assistant Examiner—Maureen M. Wallenhorst
Attorney, Agent, or Firm—Olive & Olive

[57] ABSTRACT

A cover has been designed to make a sealed chamber over a desired specimen area to control reagent evaporation which is critical for amplifying DNA in slide specimens. The cover is positioned over the specimen and temporarily adhered to, or pushed against, the slide, forming a sealed chamber. Reagents are added through a channel in the cover with a standard pipette and the channel opening is closed to prevent evaporative loss of reagents. The chamber is also designed to relieve internal vapor pressure, which is creating upon heating, thereby facilitating diffusion in and out of cells rather than allowing high pressure to flatten cells against the slide surface. Increasing the height of the chamber upwards toward a neck in the cover allows air bubbles being formed during each cycle to leave the specimen area, while at the same time preventing water vapor loss or partitioning of water vapor condensate.

6 Claims, 6 Drawing Sheets

DEVICES FOR CONTAINING BIOLOGICAL SPECIMENS FOR THERMAL PROCESSING

GOVERNMENT LICENSE RIGHTS

This invention was made with government support under GM47178 awarded by the National Institutes of Health. The government has certain rights in this invention.

CROSS-REFERENCE TO RELATED APPLICATIONS

This application is a continuation-in-part of co-pending U.S. Pat. application Ser. No. 07/836,348, filed Mar. 3, 1992, which is a national phase application based on international patent application Ser. No. PCT/US90/06768, which has a priority date of Nov. 17, 1989, based on U.S. Pat. application Ser. No. 07/438,592, issued as U.S. Pat. No. 5,188,963 on Feb. 23, 1993. The instant application is also a continuation-in-part of co-pending U.S. application Ser. No. 07/855,318 filed Mar. 23, 1992 and issued as U.S. Pat. No. 5,281,516 on Jan. 25, 1994 and co-pending U.S. Pat. application Ser. No. 07/929,720, filed Aug. 12, 1992 now abandoned, which is a divisional application of U.S. Pat. application Ser. No. 07/438,592, issued as U.S. Pat. No. 5,188,963 on Feb. 23, 1993. The disclosure of each co-pending patent application and patent referenced above and in this patent application is incorporated herein by reference.

BACKGROUND OF THE INVENTION

1. Field of the Invention

The present invention relates to the field of automated analyzers for nucleic acid diagnostics, in particular to devices which will contain the sample and reagents during thermal cycling.

2. Description of the Related Art

It is well known in the field of molecular biology that a reaction is influenced by the temperature at which the reaction is performed. If the temperature of the reaction varies, the results could be inconsistent with previous assays or with results of the calibration reactions. A device which provides heating and cooling of sample and reagents without evaporative loss is useful in many processes and particularly useful in gene amplification and detection processes. A device open to surrounding ambient air loses water vapor from aqueous fluids and, without adding water to replenish the water vapor loss, solute concentrations increase as rising temperatures drive more of the aqueous solvent from the device. It is well known in the field of molecular biology that a reaction is influenced by the concentrations of solutes in which the reaction is performed. It is also known that diffusion in and out of cells is affected by pressure. Air and vapor pressure within a sealed device increase as air and water are heated.

The device of this invention forms at least one closed chamber over a standard microscope slide or a carrier base, for example, the carrier described in U.S. Pat. application No. 5,188,963 issued Feb. 23, 1993, and pending U.S. Pat. applications Ser. No. 07/836,348 and Ser. No. 07/855,318 now U.S. Pat. No. 5,281,516 issued Jan. 25, 1994. The carrier in the aforementioned references comprises a unidirectional fluid flow channel, defined by a carrier base and a top cover portion, through which reaction fluids are introduced for complexation with target molecules of a specimen fixed to the carrier base, with the provision of a collection trough into which spent fluids drain from the carrier base.

The device of this invention may be used alone, or integrated with the carrier base supporting multiple slides, so that each chamber encloses a specimen area on the upper surface of the slides or the carrier base containing specimen holding areas. The device of this invention describes a top cover portion comprising individual chambers to be used when an evaporation-proof chamber is desired. The specimen holding area between the slide, or carrier base, and the cover are sealed for precise temperature regulation without evaporative loss of reaction fluids. Said device is interchangeable with the top cover portion as designed previously for sequential addition of a series of reagents and washes for detection.

The in situ amplification process (described in U.S. Pat. No. 5,188,963 and co-pending U.S. Pat. applications, Ser. No. 935,637, filed Aug. 24, 1992, which is a continuation of U.S. Pat. application Ser. No. 07/227,348, filed Aug. 2, 1988, now abandoned; Ser. No. 07/836,348, filed Mar. 3, 1992; and Ser. No. 07/929,720, filed Aug. 12, 1992) uses enzymes such as polymerase or ligase, separately or in combination, to repeatedly generate more copies of a target nucleic acid sequence within cells by primer extensions to incorporate new nucleotides or by ligations of adjacent complementary oligonucleotides, wherein each template generates more copies and the copies may themselves become template. By melting complementary strands of nucleic acids, the original strand and each new strand synthesized are potential templates for repeated primer annealing or ligation reactions to make and expand the number of specific, amplified products. A thermostable polymerase with reverse transcriptase activity and a thermostable ligase are now both available and increase the choice of enzymes and combination of reactions for in situ applications. If RNA in the sample is the target to be amplified, the sample is treated with reverse transcriptase to make a nucleic acid complement of the RNA just prior to amplification. Using a thermostable reverse transcriptase polymerase such as rTth (Perkin Elmer, Norwalk, Conn.), it may not be necessary to add another polymerase for rounds of primer extension amplification. The amplification can either be primer extensions in one direction for linear amplification, or in opposing directions, for geometric amplification. The label can either be incorporated as labeled nucleotides or labeled primers for one-step detection or labeled probes may be added in a step following amplification whereby the probes hybridize to the amplified products for detection.

Until in situ amplification was invented, nucleic acid amplification was limited to solution reactions wherein the nucleic acid is released from cells or tissue prior to amplification of the target sequence. In the aforementioned co-pending patent applications, a process to amplify nucleic acid targets within cells was invented and a method for embedding the cellular specimens in a matrix was described to immobilize and stabilize the cells during amplification and detection. A number of examples for using in situ amplification are given in application Ser. No. 7/438,592 now U.S. Pat. No. 5,188,963 issued on Feb. 23, 1993. A photomicrograph of cells which had amplified, labeled DNA was included in co-pending application Ser. No. 7/836,348 to show that the amplified fragments are retained in individual cells and such cells can be enumerated under microscopic observation, The process requires at least one denaturing or high temperature stage, and one primer annealing or low temperature stage in each cycle. To achieve the desired results, as stated in Ser. No. 07/836,348, the embedded cell samples are heated to nucleic acid denaturation temperature and temperature control commences before reagent addition. Since the specificity of binding one nucleic acid oligonucleotide or strand to a complementary nucleic acid is influenced by temperature, uniform and accurate temperature from sample to sample is needed for the reaction. The time required for the sample to be brought to the reaction temperatures can be a large percentage of the time allowed for the biochemical processes to be performed; therefore, means to cycle the temperature of small volumes of reagents rapidly and reliably are desirable.

It is commonly known to seal or cement cover slips to slides in order to preserve a specimen. The current techniques to prevent evaporation of reagents at elevated temperatures consist of covering the specimen, such as cells or tissue fixed on a microscope slide, with a cover slip and sealing the cover slip with either rubber cement, lacquers known commonly as finger nail polish or similar adhesives and/or overlaying the specimen with mineral oil as a vapor barrier. In the former case the adhesive bonds must be broken to remove the cover and in the latter case the mineral oil must be removed in order to continue further processing for detection. It is known in the art to use chloroform or acetone to soften hardened nail polish. These techniques are unsatisfactory because they are messy, labor-intensive and introduce unwanted material and additional steps.

Once a chamber is made with the slide or carrier base, means of adding reagents within it are necessary. Means of adding solutions to closed systems, which we have tried, include injection ports made of natural rubber (such as injection sites #75-32 from Abbott Laboratories, Ashland, Ohio), wherein reagents are injected with a standard hypodermic needle or the like. A rubber gum injection port is made so the gum material closes over the opening made by the needle when the needle is removed. These injection ports are not adaptable for automated fluid delivery probes as they require significant force to pierce. Furthermore methods using needles should be limited as handling them introduces risks to personnel.

Applying reagents with a standard pipette tip or the like is more advantageous. Flexible tubing was clamped or crimped to seal after pipetting reagents through the tubing, but sealing a small chamber with tools has difficulties. If covers are thin-walled, an injection port is as simple as making an opening in the cover by piercing the cover with a sharp point of a fluid-delivery device and then covering the opening with adhesives known in the art such as mylar tape. Mylar tape was sufficient in our experience to maintain liquids in a chamber repeatedly heated and cooled when the cover was flexible enough to vent vapor pressure. Piercing is a crude method and, since the opening must be large enough for air to escape, the reagents may leak out the opening when it is being sealed. Double bore tubing or needles may be used in which one lumen is much smaller than the other, the smaller lumen being the means by which air escapes from the chamber as fluid reagents are introduced into the chamber. The device of the invention improves on all of these possibilities by sealing the chamber, providing simple means of introducing reagents into the chamber and reclosing while also providing means to vent pressure.

Lab-Tek ® culture chamber slides (Nunc Inc., Naperyills, Ill.) are used to add growth media and an inoculum of cells for incubation in separate chambers on a microscope slide. After incubation the chamber may be separated from the slide by removing the chamber, lid and gasket in order to easily stain the cells adhering to the slide. Each Lab-Tek ® culture cheer slide is covered by setting a lid over the chamber. Ordinary air pressure and gravity provide a sufficient seal during incubations at 30–37° C. A large air space relative to the volume of media is present above the media. If such a chamber were to be used for rapid temperature cycling reactions to temperatures near 95° C., water molecules evaporating in the air space above the liquid would exert a pressure on the lid whereby the water molecules would escape the chamber or condense on the lid whose temperature is cooler than the water vapor, said water vapor removed from the reaction liquids by hanging as water droplets from the under surface of a lid. Loss of water molecules in the reaction mix with the specimen reduces or stops enzymatic activity.

The aforementioned in situ amplification for cellular analyses, which requires precise temperature regulation, creates a need for an improved apparatus which controls the temperature of the cellular specimens and prevents evaporative loss during thermal cycling. A device designed to make a reaction chamber over slide specimens such that the chamber is sealed sufficiently to prevent evaporative loss during thermal cycling, but which may be easily removed or converted to a chamber in which subsequent reagents may be added and washed away from the specimen is desirable. Thin, flat devices containing an ultra-thin specimen on its upper surface, which bottom surface makes contact with heating means, transfers and spreads the heat quickly to the specimen.

The device of this invention is a cover placed over the specimen area of the slide forming a chamber into which reagents are either placed before sealing to a slide or preferably filled after the covers are sealed to the slides. The chamber has a thin configuration over the specimen holding area to minimize the volume of reagents needed to saturate a thin specimen. Specimens are prepared to be thin for convenient microscopic analysis. The device of this invention enables and does not interfere with subsequent microscopic detection of signals within the immobilized cells or tissue specimen.

Patent applications which describe automated gene detection instrumentation and in situ sample preparation, in situ amplification and in situ detection are U.S. Pat. application Ser. No. 07/438,592, now U.S. Pat. No. 5,188,963 issued on Feb. 23, 1993 which is a continuation of U.S. Pat. application Ser. No. 07/227,348 filed Aug. 2, 1988 and now abandoned, and co-pending U.S. Pat. application Ser. No. 07/836,348, filed Mar. 3, 1992, which is a national phase application based on international patent application Ser. No. PCT/US90/06768, which has a priority date of Nov. 17, 1989, based on U.S. Pat. application Ser. No. 07/438,592, issued as U.S. Pat. No. 5,188,963 on Feb. 23, 1993; and U.S. application Ser. No. 07/855,318 filed Mar. 23, 1992 and now U.S. Pat. No. 5,281,516 issued on Jan. 25, 1994, the disclosures of all of which are incorporated herein by reference. An object of the invention is to provide a chamber for detecting molecular targets in a thin biological specimen at temperatures elevated above ambient temperature.

A further object of the invention is to temporarily seal said chamber against a discrete area of a thin specimen fixed onto a microscope slide or onto an optically clear flat base.

A yet further object of the invention is to provide means for adding and removing reaction fluids to said chamber.

A yet further object of the invention is to provide means to minimize evaporative loss of reaction fluids from said chamber.

A yet further object of the invention is to provide means to minimize pressure increases within the chamber which result form heating the chamber.

A yet further object of the invention is to either enhance a uniform refluence of water vapor back into the reaction fluids or minimize such a refluence to prevent partitioning of fluids within the chamber.

Other aspects and features of the invention will more fully apparent from a consideration of the following disclosure and appended claims.

SUMMARY OF THE INVENTION

The present invention overcomes the limitations and drawbacks described above. An earlier invention of applicant herein as discussed above contains a specimen during biochemical and molecular reactions and allows a first reagent to be added and displaced by a second reagent or wash. The device of this invention further prevents evaporative loss of reagents while rapidly bringing cellular specimens to a higher or lower predetermined reaction temperature. The device is suitable for delivery of unique fluids to individual areas of the specimens and for controlling evaporation of fluids during heating and can be readily adapted for use in an automated analyzer of DNA diagnostic tests.

In accordance with the present invention, a device for providing reagents and a controlled humidity environment for a plurality of specimens consists of a carrier base for receiving sample carriers or standard microscope slides and one or more cover holders and covers with means to make a seal between a cover and the specimen area of the slide or specimen holding area of the carrier base. A chamber is formed by sealing the cover over the specimen area. Each cover, preferably disposable, forms a chamber for an individual specimen area. It is clear to see that said covers could be formed in multiple units linking two or more together so that one molded unit provided separate chambers for different specimen holding areas of a slide or carrier base.

In one embodiment disclosed herein, the carrier base and cover holder are generally rectangular in shape and the cover holder includes a plurality of pressure plates in a linear arrangement extending downwardly therefrom, with means of aligning and pressing the covers to the specimen areas wherein each cover overlays an individual specimen area and each cover-slide pair forms a sealed humidity chamber for thermal cycling. Means of sealing include a machined or molded rim around the edge of the cover, and the said rim is placed in physical contact with the slide. Conformal or gap-filling coatings and adhesives which add resilience or stickiness, but which do not bond permanently to a slide or carrier base, may be included as means to seal the chamber. A variety of spring means may be included to apply whatever force is needed to make a watertight seal. The degree of force needed depends upon the materials of which the cover is made and/or applied at the cover rim.

Compression springs in the cover holder located between the support bar and the pressure plates provide the force to press the pressure plate against an outer edge of the cover, causing a seal to form between the downwardly extending cover rim and the slide or carrier. When the cover is sealed against the slide it provides a space extending from its inner surfaces which is coextensive with the space above the specimen, and said space becomes a humidity chamber.

It is understood that other embodiments are equally feasible such that, for example, the cover holder comprises covers arranged annularly for use in an apparatus having an annular heating plate and carrier assembly. Another possible embodiment is one in which covers, having outwardly extending threads molded or machined into them, are screwed into the cover holder; wherein the cover holder is placed in a rigid support and then the covers are turned in the reverse direction to tighten them down onto the specimen holding area.

The preferred specimen holding area is thin and flat wherein the biochemical reactions are performed in a thin aqueous film or matrix rather than in standard tube or cuvette-type containers. A specimen carrier and the fluid delivery system with which this invention may be used are further described in U.S. Pat. application No. 5,188,693. The thin, flat sample carriers are best suited for in situ DNA amplifications and detections which integrate sample collection, preparation and gene detection in one reaction vessel. In the instances where the sample-to-be-analyzed is put on a standard glass slide for the convenience of microscopic observation, a carrier base holding the slides supports the slide edges, and said carrier base or cover holder incorporates other features of a carrier such as providing a collecting trough for spent fluids. The glass slide is inserted in the carrier base which is then placed in the apparatus for processing just as carriers are positioned in racks described in U.S. Pat. No. 5,188,693. To accomplish precise heating and cooling, the invention utilizes a carrier base, of which carrier base a microscope slide may be part, where each specimen holding area of the carrier base is in communication with a heating plate as is more fully described in U.S. Pat. application Ser. No. 07/855,318 now U.S. Pat. No. 5,281,516 issued on Jan. 25, 1994. The device of the invention herein is a slide cover improving retention of aqueous fluids during thermal cycling. This slide cover may be interchangeable with other kinds of covers providing channels for unique fluid flow to each specimen. Sealing the cover against the slide or carrier base prevents loss of fluids. The chamber formed within the cover provides a thin space over the specimen in the specimen holding area whereby a small volume of reagents is spread over the surface area of the specimen area and retained during thermal cycling. The chamber is thin enough to be filled by reagents and shaped so that newly-formed bubbles migrate to the neck region and do not limit reagent availability to the specimen.

DETAILED DESCRIPTION OF THE INVENTION AND PREFERRED EMBODIMENTS THEREOF

Figure 1:
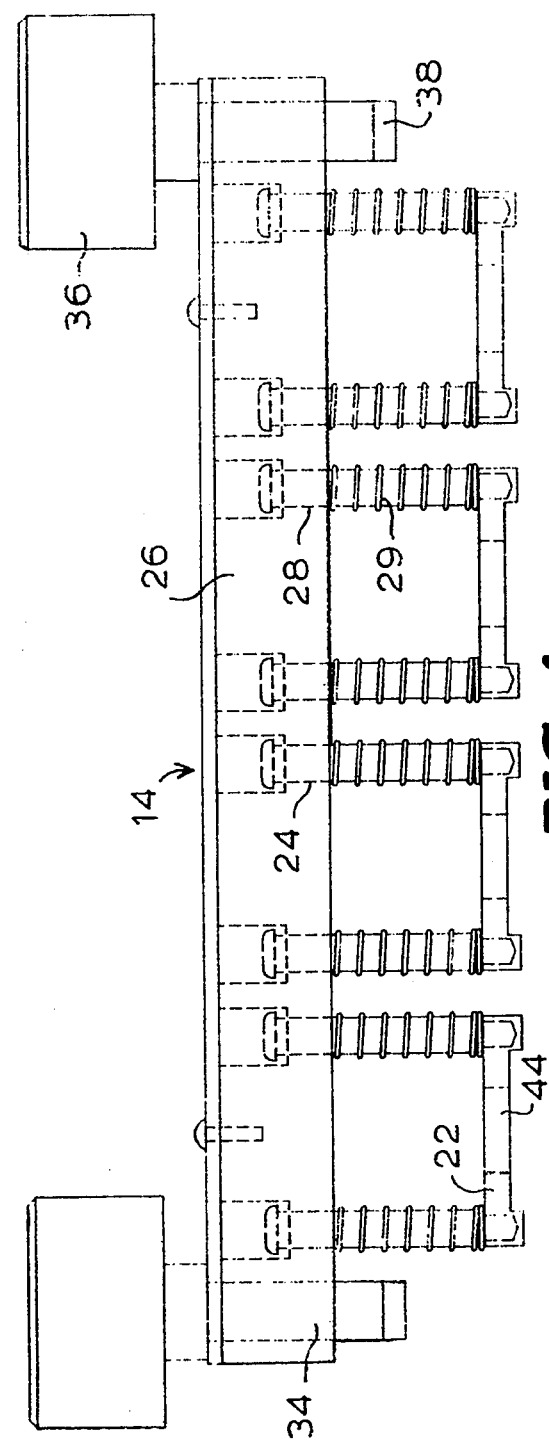
FIG. 1 is an elevational side view of a cover holder showing a support bar, pivot rods, knobs, a pair of springs in a relaxed position for each pressure plate and four pressure plates, each having an opening for a cover.

The invention broadly comprises a device 10 for processing specimens on microscope slides or similar flat devices within individual chambers temporarily placed over a desired specimen area. With reference to FIGS. 1-6, the device 10 in accordance with the present invention includes a carrier base 12, a cover holder 14 and covers 16. The carrier base 12 is preferably formed of a heat resistant material such as polycarbonate or glass or combinations thereof. The bottom of the carrier base 12 where specimens are placed on its upper surface has intimate contact with a heating platen 17. In cases where individual microscope slides 18 are placed and incorporated in the carrier base 12 to hold a specimen, openings in the carrier base 12 are provided through which openings, sections of a heating platen permit intimate contact with the bottom of the slide 18.

Standard 25 millimeter by 75 millimeter microscope slides made of glass and placed within the frame 19 become an integral part of the carrier base 12. The specimen holding area 20 covering a defined surface of a microscope slide 18, or carrier base 12, is thin so as to spread the specimen for cellular analysis. The frame 19 has grooves 21 to support the microscope slides. Individual specimens are placed in the specimen holding areas 20 of a carrier base 12 for molecular processing at precise temperatures. It is clear to see that the carrier base 12 may be formed as one structure with separate specimen holding areas 20 or as separate pieces.

The cover holder 14 has at least one pressure plate 22 and screws 24 connecting the pressure plates 22 to a support bar 26 in the cover holder 14. The screws 24 are preferably made of stainless steel and enclosed within cylindrical spring-guides 28. The means to lower and lock the cover holder 14 over the specimens may be accomplished by any number of possible assemblies but is illustrated herein by a combination of springs 29 and a rotatable locking mechanism. An alternate embodiment may comprise a cover holder comprising a molded pressure plate positioning multiple covers with a force applied by at least one leafspring. Another alternate embodiment may comprise a single molded piece incorporating the cover holder, at least one cover and a tension spring so that when external force is applied to the piece, spring tension against the cover holder presses the cover against at least one specimen area of a slide or carrier base.

Figure 2:
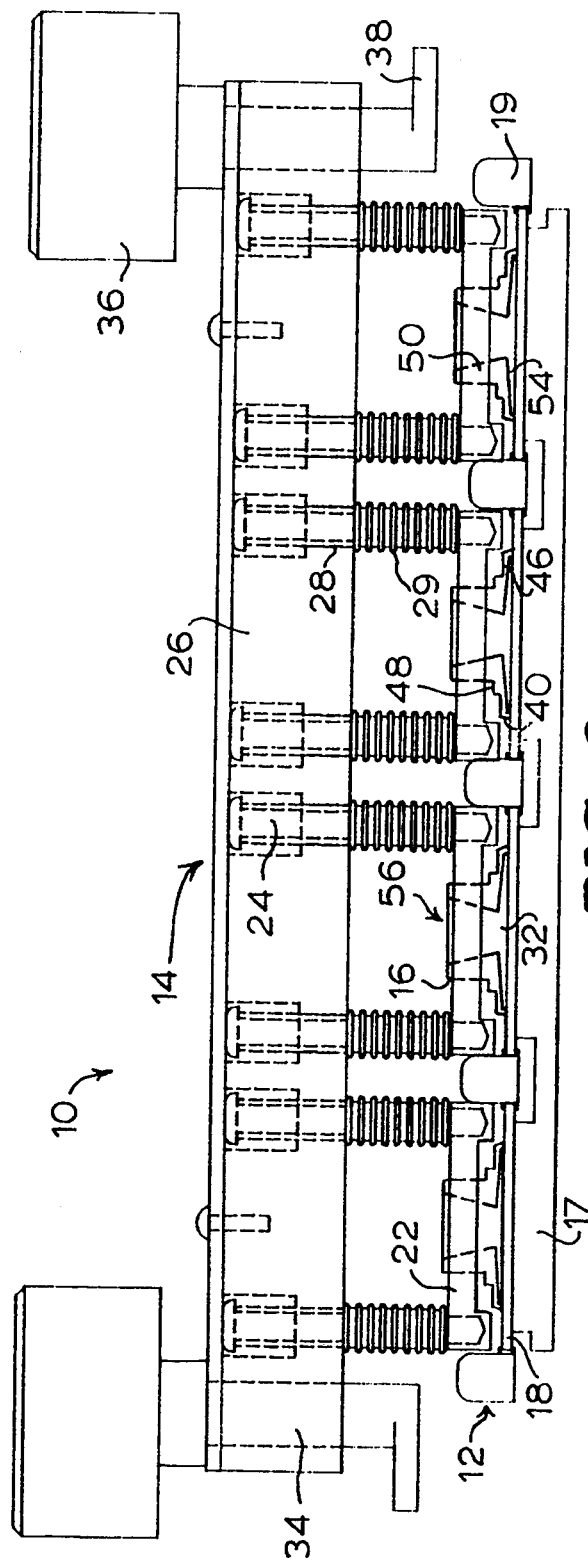
FIG. 2 is a side elevational view of the same embodiment of a cover holder as shown in FIG. 1, only showing springs compressed and the foot of each pivot rod turned to a locking position. Also shown are four covers partially inserted into the openings of the four pressure plates to illustrate the chambers formed over the specimen holding areas when the covers are pressed against microscope slides or separate carrier bases positioned in a carrier free.
Figure 3:
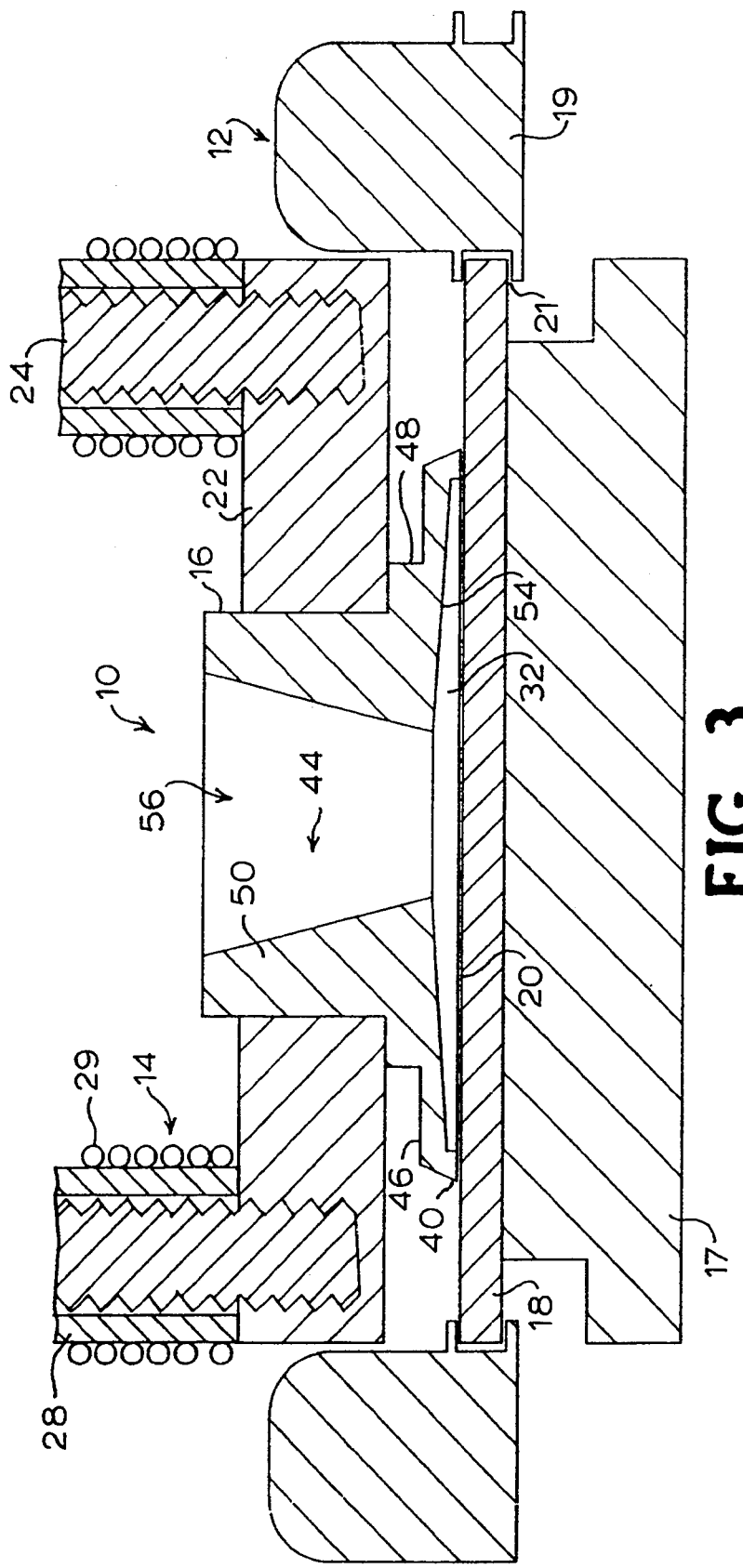
FIG. 3 is a cross-sectional view of an enlarged portion of the carrier base whose underside is in contact with a heating platen and whose upper side contains the specimen holding area and is in contact with a corresponding cover sealed over the individual specimen holding area to form a chamber.
Figure 4:
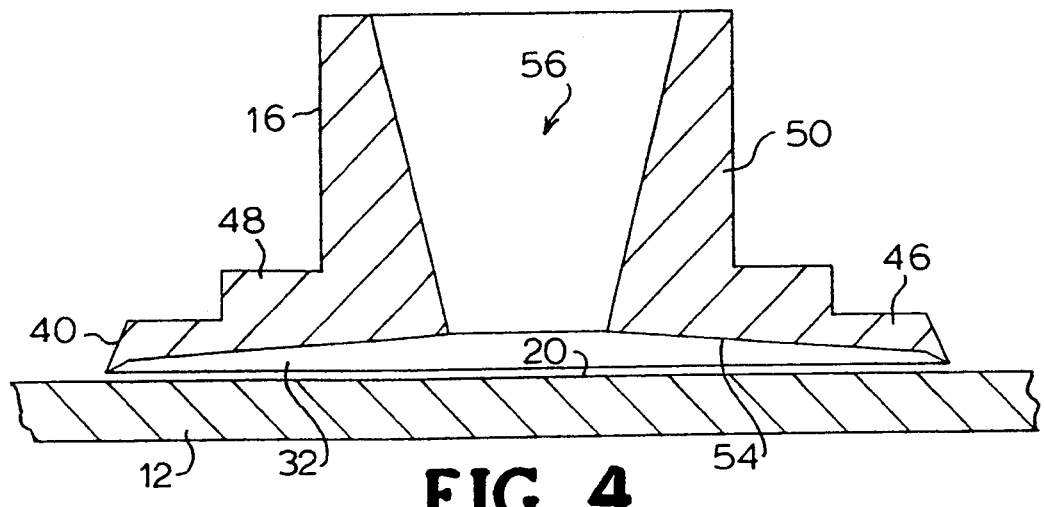
FIG. 4 is a cross-sectional view of an embodiment of a cover of the invention showing a channel into the chamber used to add liquids after sealing the cover over the specimen holding area.

In the embodiment of the carrier disclosed in FIGS. 1 and 2 herein, four specimen holding areas 20 are shown in the carrier base 12 corresponding to four pressure plates 22 on the cover holder 14. In FIG. 1 the springs 29 of the pressure plates 22 are shown relaxed. The pressure plates 22 extend from a support bar 26 and align the covers 16 over the specimen areas of corresponding slides 18 in the carrier base 12 by placing the cover holder 14 in guideposts attached and supported by an apparatus (not shown). Pressure applied to the support bar 26 of the cover holder 14 compresses the springs 29 and a locking mechanism maintains the force of the compressed springs 29 against the pressure plates 22 and the covers 16 forming a chamber 32 over the specimen holding areas 20. A locking mechanism for the spring-like action may be executed by two pivot rods 34, extending through the support bar 26, which are rotated by knobs 36 from above the support bar 26, bringing a foot 38, located at the other end of each pivot rod 34, under the each guidepost. The cover holder is held in place by the foot 38 which is stopped from movement by the underside of a guidepost. To remove the cover holder 14, the knobs 36 are turned to rotate each foot 38 free from the corresponding guidepost whereby the springs 29 decompress and the cover holder 14 may be lifted off the carrier base 12. The pressure plates 22 have some lateral movement so as to seat the cover rim 40 on the carrier base 12. The pressure plates 22 are aligned with respect to the specimens on the carrier base 12. Cover holders 14 having different configurations may be made and used according to the size or shape of the specimen on the carrier base 12 or slide 18. Disposable covers 16 likewise will be selected with a configuration which corresponds to the configuration on the pressure plates 22 to seal each chamber 32, and provide a means for adding reagents to the chamber 32.

With continued reference to FIGS. 1 and 2, the carrier base 12 is adapted to receive four standard microscope slides 18 which become part of the carrier base 12. The material-to-be-assayed which may be solid or liquid tissue specimens fixed to the upper surface of carrier base 12 at said specimen holding areas 20. The microscope slide 18 may be precoated with compounds such as aminosilane known in the art to adhere specimens to slide surfaces. Specimens may be embedded or immobilized in a matrix material on the carrier base 12.

In the embodiment shown in FIGS. 1-2 the cover holder 14 has at least one pressure plate 22 with openings 44 formed therethrough which hold or grip the covers 16. The openings 44 are aligned with respect to the specimen holding area 20 in order to position the covers 16 at desired locations.

In reference to FIGS. 1–6, a cover 16 comprises a flange 46, a step 48, and a neck 50. A cover 16 secured over the specimen holding area 20 forms a chamber 32 such that a space over the specimen is coextensive with a space under the cover 16. The vertical rise of the step 48 fits into an opening 44 securing the cover 16 in the cover holder 14 by means of a press fit. The horizontal surface of the step 48 bears the load of the cover holder 14 and presses against the cover 16, and distributes the force to the flange 46 of the cover 16 against a slide 18 or carrier base 12. The inside of the cover 16 forms a ceiling 54 for the chamber 32 over the specimen area. The neck 50 is a generally vertical portion of the chamber 32 comprising a central cylindrical channel 56 and a plug 58 to close the channel 56. The flange 46 comprises the portion of the cover 16 extending from the step 48 which makes contact with a specimen area on the slide 18 or carrier base 12. The edge of the flange 46 is designated the cover rim 40. The shape of the cover rim 40 is machined or molded to seal against the slide 18 or carrier base 12. In our experience the width of the cover rim 40 needs to accommodate the difference in coefficients of expansion when the cover 16 and the slide 18 or carrier base 12 are of dissimilar materials. Other means to enhance sealing include gaskets, conformal coatings or adhesives which may be added to the cover rim 40 to fill gaps and/or add resilience to the surface of the cover rim 40 touching the slide 18 or carrier base 12. Since the cover 16 is removable so the specimen on the slide 18 or carrier base 12 may be analyzed, the means of enhancing sealing should be temporary and coatings or adhesives are selected on the basis of characteristics making them easy to apply and to adhere to the cover rim 40, but which do not adhere permanently to the slide 18 or carrier base 12. Examples of conformal coatings are one component, self-leveling silicones (Shin-Etsu Silicones of America, Torrence, Calif.). Examples of gaskets may be O-rings of preferably 1 millimeter, or less, cross-sections which are embedded in the cover rim 40 or flat disc-like washers made of resilient material, placed to make a seal between the cover rim 40 and the specimen holding area 20.

A circular chamber with a diameter of 0.40 inch at the specimen area, for example, would be made by positioning a cover 16 with a cover rim 40 of the same internal diameter over the specimen area. The outer diameter of the flange 46 is a slightly larger diameter to make the cover rim 40 in the range of 0.010–0.030 of an inch wide. Preferably the maximum height of the ceiling 54 of the chamber 32 is 0.020 inch and slopes to a minimum height of 0.005 inch at the cover rim 40. A cover 16 of said dimensions defines a chamber 32 with a maximum holding capacity of approximately 25 microliters including filling the lower portion of the channel 56 in the neck 50. The chamber is designed to utilize small reagent volumes efficiently. Dimensions of the neck 50 are large enough to comprise a cylindrical channel having diameter of at least 0.1 inch and preferably a Luer taper having a diameter which decreases 6% from 0.176 inch to 0.152 inch from the top to the bottom of the channel 56. The outer diameter of the vertical rise between the flange 46 and the step 48 could be from 0.250 inch to 0.375 inch diameter and helps to distribute the load to the cover rim 40. The outer diameter of the neck 50 is of sufficient width to have a channel 56 within of at least 0.1 inch diameter. The neck 50 is tall enough to have the channel 56 accommodate expanding and contracting volumes during thermal cycling. A further consideration for determining the height of the neck 50 is a height that makes it easy to pick up the cover by grasping the neck. The diameters of the neck 50 and channel 56 are relatively constant although the dimensions of the step 48 and flange 46 may be smaller or larger to accommodate a smaller or larger specimen holding area 20 on the slide 18 or carrier base 12.

The covers 16 are made of a heat-resistant plastic material such as teflon, polycarbonate, polysulfone, polyetheretherketone or polypropylene and blends, welds, coatings or laminations of these and other appropriate materials. The polyetheretherketone (PEEK) material has excellent chemical and temperature resistance and has been used to machine reusable covers which were successfully tested for use in in situ DNA amplification. The surface and curing properties of materials are a significant consideration in selection because the materials need to be free of compounds or surface charges acting to bind reactants or inhibit enzymatic reactions or interfere with detection and interpretation of test results. Different materials, when used together to make a cover, need to be compatible to produce the desired characteristics.

Reagents are added to the chamber 32 through the channel 56 in the neck 50 after the cover 16 is sealed against the specimen holding area 20. The minimum channel girth was experimentally determined for convenient addition or removal of reagents. Liquid reagents are easily added to the chamber 32 through a channel 56 of at least 0.1 inch diameter by inserting a standard pipette tip or liquid delivery probe into the channel 56. Air within the chamber escapes around the pipette tip as the liquid reagents displaces it. Alternately, reagents in a dry formulation or in an agarose gel matrix may be placed in the chamber before the chamber is sealed.

In our experience the slope of the ceiling 54 of the chamber needs to have about a 3% grade for air bubbles to escape. Chambers with sloped ceilings normally fill without trapping bubbles. The chamber height is similar to capillary space that draws the liquid into it. If a small bubble does forms in the wider diameter chambers, the cover can be pressed gently and burped before plugging the channel. An objective of the chamber design is such that not only the first air in the chamber, but also any air collecting in the channel 56 upon thermal cycling, escapes into the channel 56. Because the chamber ceiling 54 slopes up to the neck 50, the neck channel 56 becomes an air space above the level of reagents in the chamber and one in which bubbles collect. It is important that air bubbles are not present in the main part of the chamber 32 which may restrict accessibility of the reagents in the specimen holding area 20 or which may partition the aqueous reagents into two parts, one containing increasing concentrations of solutes over the specimen holding area 20 because the other one part consists of water droplets condensing on the ceiling. If partitioning were to occur because newly-formed water droplets formed and did not return to mix with the initial solution, the change in molarity of solutes of the solution bathing the cells may affect biochemical and enzymatic activity. Sloping the ceiling 54 and keeping it close to the specimen holding area 20 force the air bubbles into the channel 56.

The channel 56 is closed with a plug 58 before heating the aqueous reagents to temperatures which speed up evaporation. The plug 58 needs to be secured in the channel 56 to prevent leaking and in our experience a Luer taper fit for the plug in the channel worked best, provided that the plug 58 and cover 16 materials were compatible. Since the diameter of the channel 56 is just sufficient to add reagents, regardless of the cover rim 40 diameter, the surface area of the plug 58 upon which condensation may occur is much less than the surface area of the ceiling 54. It is desirable that the surface of the channel 56 and the plug 58 have a hydrophobic character. It is our experience that condensation beads up more readily on a hydrophobic surface covering the channel 56 causing water droplets to drip back into the initial solution, thereby reducing partitioning and its consequences.

If the neck 50 and plug 58 were heated from above, it is clear that less condensation would occur on their surfaces and refluence of water vapor in the chamber 32 would be reduced. However, in the device of the invention the portion of the chamber 32 where air bubbles collect is limited to the channel 56 in the neck 50. Confining refluence to the channel 56 reduces the effect it has in the main part of the chamber 32 over the specimen holding area. Studies with cover designs in which air bubbles collected in the specimen holding area 20 resulted in cells in areas of greater reflux being more stained, thereby affecting uniformity of results. The objective of the chamber design is to confine the area of refluence and provide a uniform refluence, if it is not eliminated altogether. Filling the generally horizontal main portion of the chamber 32 with reagents and limiting air space to the generally vertical portion in the channel 56 help to achieve these objectives.

The chamber 32 is filled with a volume of reagents approaching its maximum holding capacity in order to eliminate air spaces which, when heated over the temperature ranges required for sample processing, could expand in volume more than three-fold and increase pressure in the chamber 32 an equivalent of one atmosphere. For example, a 0.40-inch diameter chamber 32 is filled with a liquid volume, preferably in the range of 25–40 microliters, and plugged so that as little air as possible remains in the chamber 32. Pressure of aqueous vapor over water increases from 17.5 millimeters of mercury (mm Hg) at 20° C. to 760 mm Hg at 100° C. (Handbook of Chemistry and Physics, Sixty-third Edition, page D197, CRC Press, Inc., Boca Raton, Fla.). If the pressure of the confined water vapor that has accumulated above its liquid is rapidly increased by heating, the pressure increase of each thermal cycle puts strain on the seal made between the cover rim 40 and the specimen holding area 20 and the seal made between the channel 56 and the plug 58. Venting the pressure puts less strain on the seals and requires less pressure to be applied to a cover 16 from the pressure plate 22. However, venting must be accomplished by means other than allowing the vapor to escape because the objective of the chamber is to maintain humidity and prevent evaporative loss.

In our experience venting the pressure within the chamber is also desirable in order that the biochemical reactions occurring in the cellular specimens and the diffusion of reagents within the chamber occur under approximately normal atmospheric pressure. While liquids themselves cannot be compressed, the cell and nuclear membranes compartmentalize cell liquids from the surrounding liquids and the increased pressure may perturb diffusion of reagents to and from the surrounding liquids in and out of the cell. In our experience we observed flattening out of cells in non-vented chambers.

Figure 5:
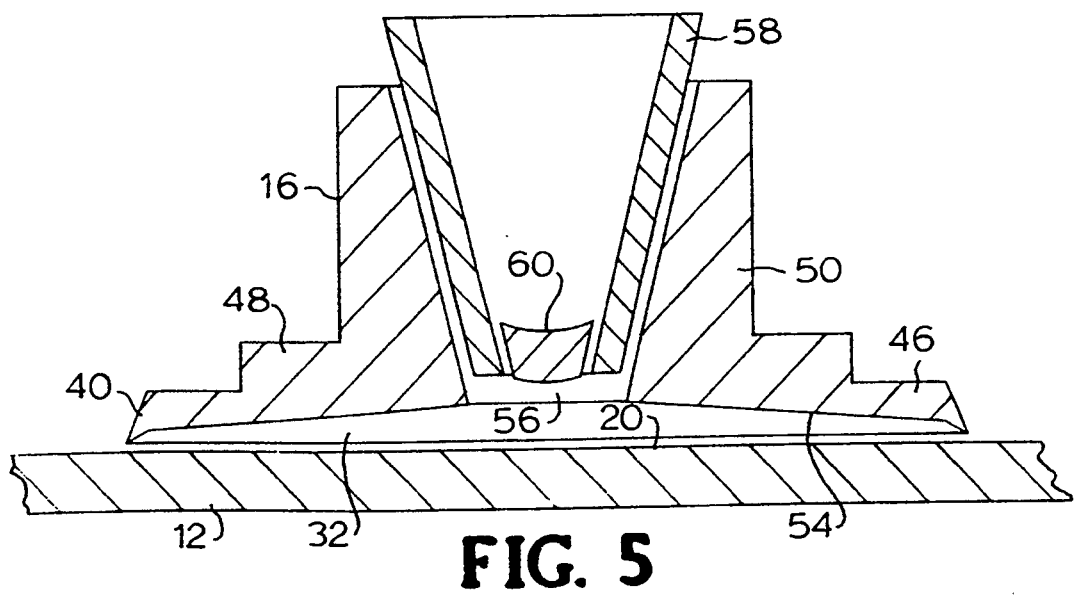
FIG. 5 is a cross-sectional view of another embodiment of a cover having a plug in the channel and a bladder in the plug to relieve pressure in the chamber.
Figure 6:
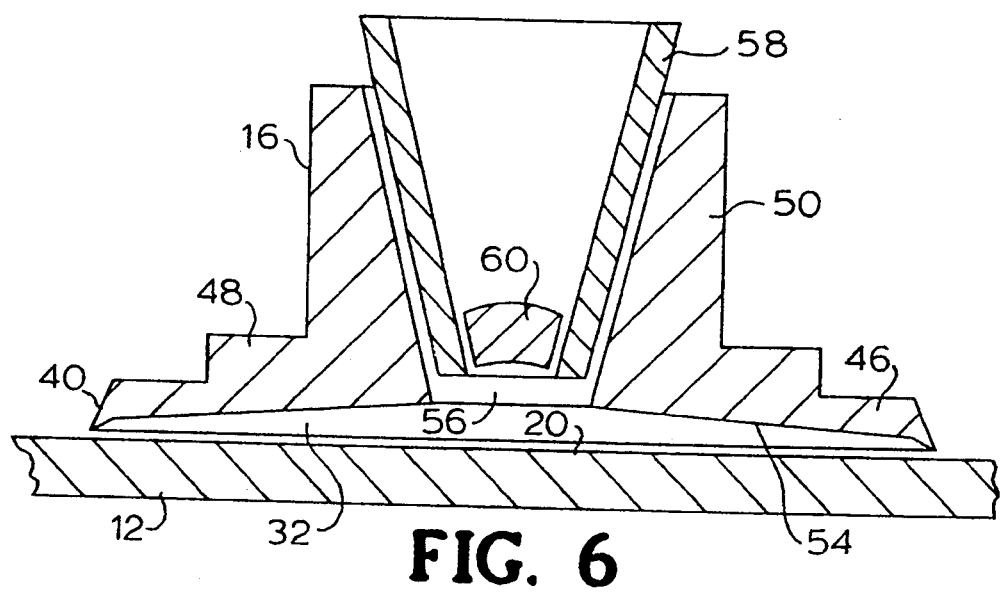
FIG. 6 is a cross-sectional view of the same embodiment of the cover as show in FIG. 5 showing a plug in the channel and illustrating the position of a bladder in the plug after internal pressure in the chamber has pushed the bladder outward to form a larger area within the chamber.

One way to vent the chamber 32 without allowing water vapor to escape is to expand the volume of the chamber 32 by incorporating a flexible portion or bladder 60 in the chamber 32. A normal pressure defines a first volume of the chamber as illustrated in FIG. 5. As the chamber contents is heated and pressure builds up, the bladder 60 bulges outward from the chamber 32 defining a second, larger volume as illustrated in FIG. 6. The chamber is heated by conductive heat from the carrier base 12 or slide 18, which heat originates from a heating plate 17 and is transferred to the carrier base 12 or slide 18. Gases rise to the neck 50 of the chamber 32 and displace any fluids in the channel 56. Water condensation droplets, which form on the undersurface of the plug 58 upon cooling, flow or drip down into main portion of the chamber 32.

In order to determine some actual volume changes that would be experienced in a chamber by vapor pressure due to heating from 25° C. to 94° C., the rise of a column of water was measured and calculated as the percent volume change and equal to the heated volume minus the original volume, divided by the original volume. The volume changes which were measured ranged from 15–30% and were affected by how much air was within the chamber after the liquids were added and by how much air was dissolved in the liquids initially. It is noted that in using the device of the invention and trying to fill the chamber with liquids and minimize the volume of air in the chamber, there are also gas molecules dissolved in the aqueous reagents being added which contribute to gas formation when the chamber is heated and cooled.

The size and shape of the bladder 60 is selected to compensate for the increased volume of reagent when it is heated. The bladder 60 may be placed within a plug 58 having a hollow core and made of an elastic material capable of being stretched over a greater surface area. In our experiments one kind of bladder 60 used was simply a thin film with an adhesive that made it stick onto the top of the neck 50 of the chamber 32. Several tapes were tested and those having a silicone adhesive or silicone/rubber blended adhesive worked well both as pressure relief and a vapor barrier. The film portion of the tape may be made of materials such as polyester, acetate or teflon. Examples of tapes used are 3M's #351 (St. Paul, Minn.) and mylar or acetate plate sealers (ICN Flow, Horsham, Pa.).

In other experiments, a bladder 60 was created by filling the hollow core of the plug 58 with a silicone gel material. The gel moved in a bladder-like manner to accommodate the changing volumes of the chamber. The silicone gels used were two-part RTV's, 6166A/B and 6196A/B mixed 1:1 (General Electric Silicones, Waterford, N.Y.). Other materials used to relieve pressure and prevent evaporation were mineral oil (Aidridge Chemical, Milwaukee, Wis.), wax pellets (Perkin Elmer, Norwalk, Conn.) and a liquid wax (MJ Research, Inc., Watertown, Mass.). The capability to prevent evaporation was increased using mineral oil or wax as plugs when combined with an adhesive film cover. The mineral oil is a less desirable means because it is difficult to remove entirely from the specimen and affects staining. Cooling the chamber 32 before removing the cover 16 solidifies the wax in the channel 56 so that when the cover 16 is removed, the wax is also physically removed from specimen holding area 20.

Alternately, venting the chamber may also be accomplished by incorporating a membranous material into the channel so that gases, except for water vapor, move in and out. A hydrophobic, extra-fine pore size, filter material #7751 (Porex, Philadelphia, Pa.) was tried and determined to be more useful when it was compressed, but not totally effective, in preventing the escape of water vapor at the temperature and pressures achieved in the chamber. If a filter material meeting the specifications of thermal cycling in the chamber is, or becomes available, it can replace adhesive films, mineral oil, waxes, and/or silicone gels.

The device of the invention provides means to add or remove reagents from a chamber and keep the chamber evaporation-proof with materials such as thin films, gels, liquids waxes, which materials are also easily pierced with automatic fluid probes. Using Luer-tapered openings in the chambers is a way to secure a tight fit for plugs containing any of the above materials. Another embodiment of the device of the invention is a cover holder molded with multiple covers aligning to the 96 wells of a standard microplate, which covers are joined in a manufacturing process of known means to corresponding wells of a microplate of the kind used in thermal cycling such as polycarbonate microplates (Techne, Princeton, N.J.). The channel in the neck of each of the microplate's 96 wells, or chambers, in the aforementioned device, made in the joining of the two pieces, comprises a Luer tapered channel. The plugs fitting these Luer tapered channels may also be molded with a support that aligns the plugs in 96-well array. It is our experience that the silicone gel A and B components can be mixed and dripped into male Luer connections which have been cut off the end of a standard syringe. The gel will not flow through the Luer connection but cures within it. After curing the silicone, Luer connections placed in Luer-tapered channels provide a vapor barrier that can be penetrated for automated fluid exchanges. The usefulness of the device of the invention is that the vapor barrier material may be placed in the plugs as part of the manufacturing process. A microplate format with 96 multiple specimen chambers joined to covers comprising corresponding 96 Luer-tapered openings are therefore capable of being sealed snugly with a single 96-multi-plug piece for thermal cycling. The advantage is that there is no carryover of material from one of the well chambers to another and products of each reaction can be recovered without removing the covers or plugs.

The carrier base 12 and cover holder 14 may be closed together by a spring-loaded closure before placing them in the temperature apparatus. Another embodiment of a cover holder 14 may have the means to grip or snap directly onto an individual microscope slide 18 and in this embodiment the heating platen 17 would be configured to enable part of the cover holder 14 to extend underneath the edge of the microscope slide 18. It is clear that positioning cover holders and covers could be automated. It is also clear to see that the specimen holding areas may be integral parts of a multi-cavity molded carrierbase rather than separate glass slides. Also within the scope of the invention are chambers which accommodate larger tissue specimens, or multiple chambers per slide to accommodate two or more specimens on the same slide, or the addition of different reagent sets to duplicate specimen samples on the same slide. While diameter dimensions indicate the chambers 32 described herein cover a circular part of the specimen holding area 20, it is clear that elliptical or other shapes are equally useful.

Figure 7:
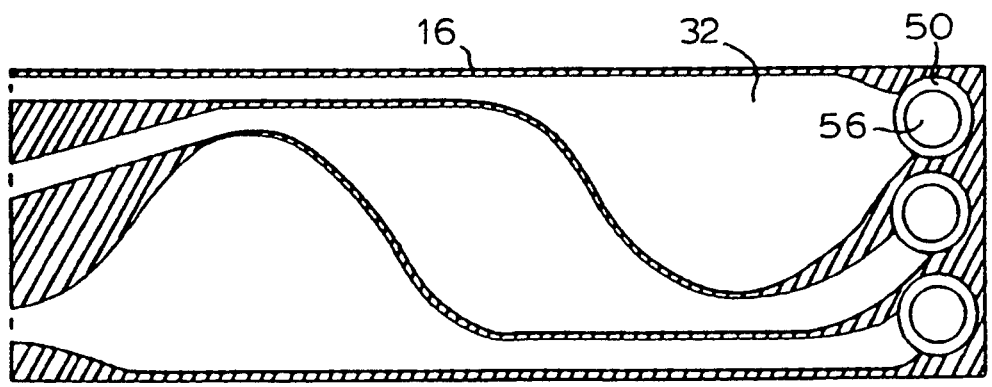
FIG. 7 is a diagrammatic sketch of the top view of a cover capable of forming three chambers and a separate fluid-flow channel leading to and away from each of the three chambers.

Another embodiment of a cover is a configuration forming channels leading to and away from individual chambers when the cover is pressed against a slide or carrier base. This embodiment illustrates a way to integrate the carrier described in U.S. Pat. No. 5,188,963 with the device of this invention. In our research, several designs were outlined with adhesive on different slides and after placing covers over the outlines, each design was tested for uniform flow to three specimen areas on one slide through three separate channels. The design selected by its capability for fluids to flow through best without air blocks is illustrated in FIG. 7. It is understood that various cover configurations may be made to match the desired surface area of the specimen holding area to-be-included in the chamber and such chambers would also have means for sealing and venting for thermal cycling.

In summary, the device of the invention provides an evaporation-proof chamber to use with a temperature-controlled apparatus enabling in situ sample preparation, DNA amplification, DNA hybridization or other complexation of specific molecules within biological specimens for clinical diagnoses of said biological specimens, wherein said biological specimens are contained on specimen holding areas of a microscope slide, a carrier base or in a 96-well plate. The chambers are formed by pressing or sealing a cover holder against a cover and onto said slide, carrier base or 96-well plate.

Other modifications of the above-described embodiments of the invention as used by those of skill in the mechanical arts and related disciplines are intended to be within the scope of the invention.

What is claimed is:

1. A chamber device for detecting molecular targets in a biological specimen at temperatures elevated above ambient temperature, comprising:
    (a) a microscope slide having a flat specimen area containing a biological specimen;
    (b) a cover covering said flat specimen area; said cover comprising a flange which sealingly contacts the microscope slide about the flat specimen area, a ceiling connected to the flange and a neck which protrudes upwardly from the ceiling;
    (c) said cover and said flat specimen area forming an enclosure having an interior space comprising a chamber device that prevents evaporative loss of reaction fluids;
    (d) said neck in said cover having a channel for adding reaction fluids to said chamber device and removing reaction fluids from said chamber device after said enclosure is formed; and
    (e) means for closing said channel to provide a water vapor barrier in said chamber device.

2. A chamber device for detecting molecular targets in a biological specimen according to claim 1, further comprising a means to make a temporary, watertight seal between said cover and said flat specimen area of said microscope slide; wherein the sealing means have characteristics allowing the cover to be removed from the microscope slide.

3. A chamber device for detecting molecular targets in a biological specimen according to claim 2, wherein said means to make a watertight seal is selected from the group consisting of spring tension, gaskets, conformal coatings and adhesives.

4. A chamber device for detecting molecular targets in a biological specimen according to claim 1, further comprising:

(a) means for sealing said channel to minimize evaporative loss of reaction fluids, said means for sealing being selected from a group consisting of adhesives and plug structures which exclude water vapor from exiting the chamber device through the channel;

(b) means for minimizing pressure increases in said chamber device selected from the group consisting of cover materials located in said channel which are capable of expanding the volume capacity of the chamber device and membranes located in said channel which are capable of venting air but not water vapor from the chamber device; and (c) means for enhancing a uniform refluence of water vapor to reaction fluids in said chamber device selected from the group consisting of overlayering aqueous reagents in the chamber device with oil or wax materials, a sloped chamber device ceiling and hydrophobic surface material on the chamber device ceiling; wherein said biological specimen can be viewed microscopically.

5. A chamber for detecting molecular targets in a biological specimen according to claim 1, further comprising means for providing pressure relief in said chamber device when said chamber device is repeatedly heated to about 90°.

6. A chamber for controlling evaporation of aqueous reagents when said aqueous reagents are repeatedly heated to temperatures of about 90° C. which cause rapid increases in water vapor pressure; comprising, (a) a specimen holding area, said specimen holding area defined as an area on a flat surface of an optically clear material;

(b) a cover having a rim affixed to the specimen holding area to enclose a specimen in a chamber; said chamber comprising a ceiling of a sufficient height to allow diffusion of aqueous-based reagents within the specimen positioned in the specimen holding area; said ceiling having an upward slope allowing air bubbles to rise;

(c) said rim having means to seal said cover at the specimen holding area to hold liquid reagents in said chamber;

(d) said chamber further comprising a neck protruding upwardly from the ceiling having a channel of sufficient girth to allow air in the chamber to escape when liquid reagents are added after the chamber is formed;

(e) said channel being sealed by a closure selected from a group consisting of self-sealing means provided as part of the cover and separate closure devices; wherein said channel provides a space for rising air bubbles to collect away from said specimen holding area and wherein said closure makes a vapor-tight seal in the channel of said cover; and (f) said cover and closure having the structural capability to contain water vapor with increasing water vapor pressure due to heating aqueous reagents within the chamber.

* * * * *

UNITED STATES PATENT AND TRADEMARK OFFICE
CERTIFICATE OF CORRECTION

PATENT NO. : 5,346,672

DATED : September 13, 1994

INVENTOR(S) : Marilyn J. Stapleton, Villette S. Thorpe, Warren R. Jewett

It is certified that error appears in the above-indentified patent and that said Letters Patent is hereby corrected as shown below:

Column 4, line 11, replace "cheer" with --chamber--.

Signed and Sealed this

Twenty-seventh Day of December, 1994

Attest:

BRUCE LEHMAN

Attesting Officer

Commissioner of Patents and Trademarks